(12) United States Patent
Burton et al.

(10) Patent No.: US 7,612,248 B2
(45) Date of Patent: Nov. 3, 2009

(54) ABSORBENT MEDICAL ARTICLES

(75) Inventors: Scott A. Burton, Woodbury, MN (US); Steven C. Stickels, Woodbury, MN (US); Matthew T. Scholz, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1295 days.

(21) Appl. No.: 10/324,832

(22) Filed: Dec. 19, 2002

(65) Prior Publication Data

US 2004/0133143 A1 Jul. 8, 2004

(51) Int. Cl.
*A61F 13/00* (2006.01)

(52) U.S. Cl. .............. 602/58; 602/42; 602/43; 602/54

(58) Field of Classification Search ............. 602/41–59; 424/443–449; 128/888, 889
See application file for complete search history.

(56) References Cited

U.S. PATENT DOCUMENTS

| | | | | |
|---|---|---|---|---|
| RE24,906 E | 12/1960 | Ulrich | | 206/59 |
| 3,121,021 A | 2/1964 | Copeland | | 117/122 |
| 3,389,827 A | 6/1968 | Abere et al. | | 220/53 |
| 4,112,213 A | 9/1978 | Waldman | | 526/279 |
| 4,360,015 A | 11/1982 | Mayer | | 128/156 |
| 4,499,896 A | 2/1985 | Heinecke | | 128/156 |
| 4,598,004 A | 7/1986 | Heinecke | | 428/40 |
| 4,738,257 A | 4/1988 | Meyer et al. | | 128/156 |
| 4,849,458 A | 7/1989 | Reed et al. | | 521/159 |
| 4,901,714 A | 2/1990 | Jensen | | 128/156 |
| 4,909,244 A | 3/1990 | Quarfoot et al. | | 128/156 |
| 4,935,087 A | 6/1990 | Gilman | | 156/251 |
| 4,957,795 A | 9/1990 | Riedel | | 428/74 |
| 5,010,883 A | 4/1991 | Rawlings et al. | | 128/155 |
| 5,018,515 A | 5/1991 | Gilman | | 128/155 |
| 5,501,661 A | 3/1996 | Cartmell et al. | | 602/58 |
| 5,512,041 A | 4/1996 | Bogart | | 602/58 |
| 5,527,535 A | 6/1996 | Guillemet | | 424/443 |
| 5,531,855 A | 7/1996 | Heinecke et al. | | 156/252 |
| 5,603,946 A | 2/1997 | Constantine | | 424/445 |
| 5,614,310 A | 3/1997 | Delgado et al. | | 428/316.6 |

(Continued)

FOREIGN PATENT DOCUMENTS

EP     0 099 748 A1    2/1984

(Continued)

*Primary Examiner*—Kim M Lewis

(57) ABSTRACT

Medical articles including an absorbent layer, a backing layer and an optional liquid permeable facing layer are disclosed. The construction of the medical article is such that volumetric expansion of the absorbent layer is allowed in directions parallel to the surface of the backing layer as the absorbent layer absorbs moisture. The medical article may include a debonding agent located between the absorbent layer and the backing layer. The absorbent layer is operably attached to the backing layer. When the absorbent layer absorbs moisture, e.g., wound exudate, at least a portion of the absorbent layer detaches from the backing layer such that the absorbent layer can expand and move relative to the backing. The debonding agent facilitates this change from attachment to detachment of the absorbent layer to the backing. The medical articles of the present invention may also be constructed such that a portion of the front surface of the backing layer located directly opposite the absorbent layer is free of adhesive. The adhesive free area or areas may be provided in place of a physical debonding agent or in addition to a physical debonding agent.

111 Claims, 5 Drawing Sheets

U.S. PATENT DOCUMENTS

| | | | |
|---|---|---|---|
| 5,653,699 A | 8/1997 | Reed et al. | 604/307 |
| 5,733,570 A | 3/1998 | Chen et al. | 424/445 |
| 5,738,642 A | 4/1998 | Heinecke et al. | 602/58 |
| 5,849,325 A | 12/1998 | Heinecke et al. | 424/443 |
| 5,931,800 A | 8/1999 | Rasmussen et al. | 602/57 |
| 5,968,001 A | 10/1999 | Freeman | 602/42 |
| 6,103,369 A | 8/2000 | Lucast et al. | 428/354 |
| 6,171,985 B1 | 1/2001 | Joseph et al. | 442/346 |
| 6,175,054 B1 | 1/2001 | Jacques | 602/48 |
| 6,198,016 B1 | 3/2001 | Lucast et al. | 602/41 |
| 6,326,410 B1 | 12/2001 | Cheong | 521/67 |
| 6,420,622 B1 | 7/2002 | Johnston et al. | 602/41 |
| 6,566,575 B1 * | 5/2003 | Stickels et al. | 602/41 |
| 6,607,739 B1 * | 8/2003 | Wallo | 424/404 |
| 2001/0051178 A1 | 12/2001 | Blatchford et al. | 424/443 |
| 2003/0203010 A1 * | 10/2003 | Wallo | 424/443 |

FOREIGN PATENT DOCUMENTS

| | | |
|---|---|---|
| EP | 0 257 133 A2 | 3/1988 |
| EP | 0 264 299 B2 | 4/1988 |
| EP | 0 341 870 A2 | 11/1989 |
| EP | 0 457 977 A1 | 11/1991 |
| WO | WO97/42917 | 11/1997 |
| WO | WO98/17328 | 4/1998 |
| WO | WO 99/06077 | 2/1999 |
| WO | WO 99/13865 | 3/1999 |
| WO | WO 00/42958 | 7/2000 |
| WO | WO 01/60296 A1 | 8/2001 |
| WO | WO 02/20067 A2 | 3/2002 |

* cited by examiner

ABSORBENT MEDICAL ARTICLES

BACKGROUND

The present invention is directed to medical articles incorporating absorbent layers, particularly medical articles useful as wound dressings.

Historically, exudate from a wound has been treated by absorbing it using a dressing containing an absorbent material. Typical such dressings contain a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

More recently the use of so-called "occlusive" dressings for pressure sores and ulcers has gained increasing acceptance. A number of wound dressings of this kind are commercially available. Most of these products are formed from several layers, including at least an inner skin-contacting layer and an outer backing layer. The dressing is applied as a cover for the sore or ulcer in a size providing a margin around the wound area that adhesively seals to the skin. The inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

A wound care product in current use utilizes a hydrocolloid absorbent. Such a material typically has poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

There are known hydrophilic gel materials useful in medical applications such as wound dressings, however, many of them do not have the appropriate balance of absorption and cohesive strength often needed. Thus, additional such materials are needed. Furthermore, it be desirable to provide an occlusive material that is also transparent and flexible for use in a medical article such as a wound dressing or wound packing material.

Another issue that arises in connection with medical articles incorporating absorbent layers is the volumetric expansion of the absorbent materials. When the absorbent layers are attached to, e.g., a backing, expansion of the absorbent layer in directions parallel to the surface of the backing are constrained as the absorbent layer absorbs moisture. As a result, the swelling absorbent layer can stretch the backing and may also pull away from the plane of the skin to form a bubble or a tent above a wound. The swollen wound dressing increases the profile or thickness of the dressing, thus potentially increasing the shearing forces exerted on the dressing by clothing or bedding.

SUMMARY OF THE INVENTION

The present invention provides medical articles including an absorbent layer located between a backing layer and an optional liquid permeable facing layer. The construction of the medical article is such that volumetric expansion of the absorbent layer is allowed in directions parallel to the surface of the backing layer as the absorbent layer absorbs moisture. As a result, localized stretching of the backing layer may be reduced.

In one set of embodiments of medical articles of the present invention, the medical article includes a debonding agent located between the absorbent layer and the backing layer. The absorbent layer is operably attached to the backing layer before the medical article is used. After, however, the absorbent layer absorbs sufficient moisture, e.g., wound exudate, at least a portion of the absorbent layer detaches from the backing layer such that the absorbent layer can expand and move relative to the backing. The debonding agent facilitates this change from attachment to detachment of the absorbent layer to the backing.

It may, e.g., be preferred that the absorbent layer is at least partially detached from the backing layer when the absorbent layer has absorbed 100 wt-% or more of water. It may be more preferred that at least partial detachment of the absorbent layer from the backing layer occur when the absorbent layer has absorbed 200 wt-% or more of water, in some instances, 300 wt-% or more of water.

In other embodiments, the medical articles of the present invention may be constructed such that a portion of the front surface of the backing layer located directly opposite the absorbent layer is free of adhesive. The adhesive free area or areas may be provided in place of a physical debonding agent, although in some instances it may be desirable to include both adhesive free areas and one or more physical debonding agents.

By allowing at least portions of the absorbent layer to detach from the backing in the presence of water (or aqueous solutions such as wound exudate), stretching of the backing and resulting increases in the profile of, e.g., a medical dressing above a wound may be reduced. As a result, integrity in the adhesion of such medical dressings to a patient's skin may be improved.

The debonding agent may be water soluble or water insoluble, although it should be understood that the solubility of a water soluble debonding agent need not be complete. For example, it may be possible that the debonding agent only partially solubilizes in the presence of water such that at least a portion of the absorbent layer detaches from the backing. Further, unless otherwise explicitly indicated, water swellable may preferably be considered as included within the definition of water soluble for the purposes of the present invention (provided that a water swellable debonding agent provides the same functional detachment of the absorbent layer from the backing layer as described herein).

It may be preferred that the debonding agent exhibit sufficient water solubility such that at least a portion of the absorbent layer detaches from the backing only at or near human body temperature (e.g., 35 degrees Celsius or higher), but remain substantially water insoluble at temperatures of 30 degrees Celsius or less.

Another manner in which the solubility of the debonding agent may be characterized is by its solubility in the presence of wound exudate. The debonding agent may be soluble in the presence of wound exudate, although it should be understood that the solubility of the debonding agent in the presence of wound exudate need not be complete. For example, it may be possible that the debonding agent only partially solubilizes in the presence of wound exudate such that at least a portion of the absorbent layer detaches from the backing. It may be preferred that the debonding agent exhibit sufficient solubility in the presence of wound exudate such that at least a portion of the absorbent layer detaches from the backing only at or near human body temperature (e.g., 35 degrees Celsius or higher), but remain substantially insoluble in the presence of wound exudate at temperatures of 30 degrees Celsius or less.

Examples of some suitable debonding agents include, but are not limited to, articles such as continuous and non-continuous films, foam, etc. The debonding agents may be in the form of fibrous structures such as netting, fabrics (nonwoven, woven, knit, etc.), etc. The debonding agent may be water soluble or water insoluble.

Examples of water soluble films that may be used as a debonding agent in medical articles of the present invention include, but are not limited to, polyvinylpyrrolidone, polyvinylalcohol, hydrophilic polyurethanes, hydrophilic hydroxyalkylesters of poly(meth)acrylic acid and copolymers thereof, and hydrophilic polyether-polyamide polymers. The water soluble films may or may not be coextensive with the absorbent layer.

Debonding agents used in medical articles of the present invention may also include particulate material including, but not limited to, e.g., inorganic particles such as colloidal silicon dioxide, organic particles such as carboxymethylcellulose, etc. The particulates may be water soluble or water insoluble.

Debonding agents used in connection with the present invention may also include combinations of different articles and/or particulates provided that the desired detachment of the backing and the absorbent layer can be achieved in the presence of water.

The medical articles of the present invention may preferably include a facing layer (preferably, a liquid permeable facing layer) and a backing layer (preferably, a moisture vapor permeable backing layer) with the absorbent layer located between the facing layer and the backing layer. The backing layer may preferably be moisture vapor permeable but liquid impermeable. The medical article, e.g., wound dressing, may further include a layer of pressure sensitive adhesive to secure the article to the skin.

In some embodiments of the present invention, the facing layer may occupy a smaller area than the backing layer such that the backing layer extends beyond the periphery of the facing layer to form a frame about the facing layer. In such a configuration, the edges of the medical article may be more compliant and provide a lower edge profile than if the facing layer and the backing layer were coextensive with each other. That improved compliance and lower edge profile can be beneficial in preventing unwanted detachment of the edge of the medical article from a patient due to stretching of the skin or friction from garments or bedding. Furthermore, moisture vapor permeability in the frame formed by the backing layer may also be increased, thereby improving adhesion and comfort of the medical article.

As used herein the terms "front surface" and "back surface" used with respect to the absorbent layer, the facing layer, the backing layer, and any other components in the medical articles, refer to the major surface of the indicated component that, in use, faces toward the wound surface or away from the wound surface, respectively.

Although the absorbent layers shown in connection with the illustrative embodiments of the invention are depicted as homogeneous, unitary layers, it should be understood that the absorbent layers may be non-homogeneous. For example, the absorbent layers may include two or more different materials, be composite structures of separate articles, etc.

The absorbent layers used in medical articles according to the present invention may be, e.g., polymeric gel materials that are preferably absorbent, and more preferably absorbent and transparent. By "gel" (or "polymer gel" or "polymeric gel material" or "hydrophilic gel") it is meant a gel material capable of swelling on contact with (or water-based fluids such as body fluids including blood, plasma, and intracellular fluid or fluids similar to body fluids such as physiological saline), but does not dissolve in, water. The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is preferably capable of absorbing fluids, particularly body fluids and preferably moderate to heavy amounts of body fluids, while retaining its structural integrity (i.e., remaining sufficiently intact such that it can perform the function of acting as an absorbent moist wound healing dressing, for example), and preferably its transparency. By "transparent" it is meant that when the preferred material is applied to a patient (e.g., at a wound site), the area underlying the dressing can be visualized sufficiently to permit observation of the wound by a health care worker.

The application of water swelling polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, "medical" applications encompasses dental applications, including dental adhesives, restoratives, coatings, composites, sealants, etc. Because water swelling polymer gels have compositions and mechanical properties similar to those of biological tissues, such gels may be applied in a wide variety of fields in the future.

In one aspect, the present invention provides a medical article including a backing layer having backing adhesive on a front surface of the backing layer; a liquid permeable facing layer; an absorbent layer located between the backing layer and the facing layer, wherein a back surface of the absorbent layer faces the front surface of the backing layer; and a water soluble film located between the front surface of the backing layer and the back surface of the absorbent layer.

In another aspect, the present invention provides a medical article including a backing layer having backing adhesive on a front surface of the backing layer; a liquid permeable facing layer; an absorbent layer located between the backing layer and the facing layer, wherein a back surface of the absorbent layer faces the front surface of the backing layer; and a debonding agent located between the front surface of the backing layer and the back surface of the absorbent layer. The back surface of the absorbent layer is operably attached to the front surface of the backing layer before the medical article is applied to a patient, and at least a portion of the back surface of the absorbent layer is detached from the front surface of the backing layer when the absorbent layer has absorbed 100 wt-% or more of water.

In another aspect, the present invention provides a medical article including a moisture vapor permeable backing layer with backing adhesive on a front surface of the backing layer; a liquid permeable facing layer in the form of a film that includes a plurality of openings formed therethrough and facing adhesive on a front surface of the facing layer, wherein the backing layer and the backing adhesive extend past a perimeter of the facing layer such that the backing layer and the backing adhesive form a frame about the periphery of the facing layer. The medical article further includes an absorbent layer located between the backing layer and the facing layer, wherein a back surface of the absorbent layer faces the front surface of the backing layer, wherein a back surface of the facing layer is attached to the front surface of the backing layer about a periphery of the absorbent layer, and wherein the absorbent layer is substantially free of water before the medical article is applied to a patient. The medical article also includes a water soluble debonding agent located between the front surface of the backing layer and the back surface of the absorbent layer. The back surface of the absorbent layer is operably attached to the front surface of the backing layer before the medical article is applied to a patient, and at least a portion of the back surface of the absorbent layer is detached from the front surface of the backing layer when the absorbent layer has absorbed 100 wt-% or more of water. The combination of the backing layer, the facing layer, the absorbent layer, and the debonding agent are transparent when the absorbent layer has absorbed 100 wt-% isotonic saline solution.

In another aspect, the present invention provides a medical article including a backing layer having backing adhesive on a front surface of the backing layer; an absorbent layer located proximate the front surface of the backing layer, wherein a back surface of the absorbent layer faces the front surface of the backing layer; and a debonding agent located between the front surface of the backing layer and the back surface of the absorbent layer. The back surface of the absorbent layer is operably attached to the front surface of the backing layer before the medical article is applied to a patient, and at least a portion of the back surface of the absorbent layer is detached from the front surface of the backing layer when the absorbent layer has absorbed 100 wt-% or more of water.

In another aspect, the present invention provides a medical article including a backing substrate; a liquid permeable facing layer; an absorbent layer located between the backing substrate and the facing layer, wherein a back surface of the absorbent layer faces the front surface of the backing substrate; and backing adhesive on the front surface of the backing substrate, wherein the backing adhesive occupies an edge zone on the front surface of the backing substrate surrounding the absorbent layer, and further wherein a portion of the front surface of the backing substrate located directly opposite the absorbent layer is free of the backing adhesive.

These and other features and advantages of the invention may be described below with respect to various illustrative embodiments of the invention.

BRIEF DESCRIPTIONS OF THE FIGURES

DETAILED DESCRIPTION OF ILLUSTRATIVE EMBODIMENTS OF THE INVENTION

In the following detailed description of illustrative embodiments, reference is made to the accompanying drawings that form a part hereof, and in which are shown, by way of illustration, illustrative embodiments in which the invention may be practiced. It is to be understood that other embodiments may be utilized and structural changes may be made without departing from the scope of the present invention.

Medical articles, particularly wound dressings, of the present invention may advantageously remove excess exudate from a wound; maintain a moist wound environment; allow gas exchange so that oxygen, water vapor, and carbon dioxide can pass through the medical article; are thermally insulating to maintain the wound at body temperature. The medical articles may be impermeable to liquids and microorganisms to minimize contamination and infection; may be non-adherent to the wound so that no damage is done to the granulating tissue; and may minimize the need to cleanse the wound of dressing material.

It may be preferred that the medical articles of the present invention be transparent so that the wound site to which they are applied can be viewed through the medical article. It is advantageous to view and evaluate the wound and healing thereof without removal of the medical article to avoid unnecessary disruption of the wound site and exposure of the wound to the environment, which reduces the likelihood of contamination, and avoids the need to cleanse the wound as would be the case were the medical article to be removed. It may be further preferred that the medical article be both transparent and colorless so that the color of the wound, exudate, and periwound skin may also be evaluated.

With the exception of the debonding agents or layers in the medical articles of the present invention, the various components of the medical articles may be similar to, or the same as, those described in U.S. patent application Ser. No. 10/121,518, filed on 12 Apr. 2002, titled GEL MATERIAL, MEDICAL ARTICLES, AND METHODS. The components used in the medical articles of the present invention should not, however, be limited by the descriptions of the corresponding components recited in that application.

Figure 1:
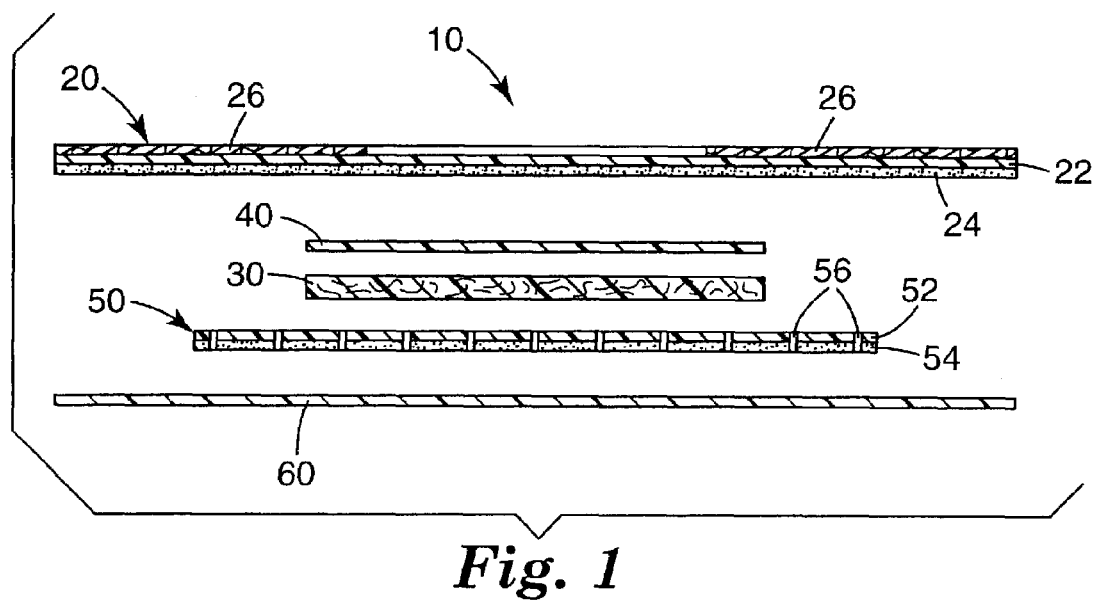
FIG. 1 is an exploded cross-sectional view of one illustrative embodiment of a medical article according to the present invention.

FIG. 1 is an exploded cross-sectional view of one medical article 10 that may be useful as, e.g., a wound dressing. The article 10 includes a backing layer 20, absorbent layer 30, debonding agent 40, optional facing layer 50, and optional release liner 60. The release liner 60 is provided mainly to protect the medical article 10 until it is applied to a patient. As a result, the release liner 60 is located on the front surface of the medical article.

The backing layer 20 includes a backing substrate 22 on which backing adhesive 24 is located. The debonding agent 40, in the depicted embodiment, is a continuous layer located between the absorbent layer 30 and the backing layer 20. In the depicted embodiment, the debonding agent 40 is attached to the front surface of the backing layer 20 by the backing adhesive 24. The debonding agent 40 is also preferably attached the back surface of the absorbent layer 30 such that the absorbent layer 30 is operably attached to the backing layer 20.

As used herein, "operably attached" includes methods of attachment in which the two recited components are directly attached to each other (i.e., in physical contact) as well as when the two cited components are attached to each other through one or more intermediate components (such as in the depicted embodiment in which absorbent layer 30 is operably attached to the backing layer 20 through debonding agent 40).

Also depicted in FIG. 1 is an optional frame 26 on the back surface of the backing layer 20 to provide temporary support to the medical article 10 during application. Frame 26, if present, is generally removably adhered to the backing layer to facilitate removal after application of the medical article to a wound site. The frame 26 may preferably be made of a relatively rigid material that maintains the shape of the medical article during handling and application to the wound site. Examples of some suitable frames are described in, e.g., U.S. Pat. No. 5,531,855 (Heinecke et al.) and U.S. Pat. No. 5,738,642 (Heinecke et al.).

The optional facing layer 50 depicted in FIG. 1 includes a facing substrate 52 and a layer of facing adhesive 54 on the front surface of the facing layer 52 (i.e., the surface facing the release liner 60). The facing layer 50 is liquid permeable to, e.g., allow the passage of liquid wound exudate. The depicted embodiment includes a apertures 56 formed through the facing layer 50 to conduct exudate from the wound surface to the absorbent layer 30. Although the apertures 56 are depicted as voids in the facing layer 50, they may also be provided as slits or other openings sufficiently large to provide for the passage of liquid through the facing layer 50 to the absorbent layer 30.

The facing adhesive 54 is optionally included to assist in securing the medical article to the patient. As depicted, the facing adhesive 54 is substantially coextensive with the facing layer 50, i.e., the facing adhesive covers substantially the entire wound-facing surface of facing layer 50. In such constructions, it will be understood that the apertures 56 would preferably extend though both the facing substrate 52 and the facing adhesive 54 as shown. It will be understood, however, that facing adhesive 54 may not be provided or may be provided on only a portion of the facing substrate 52. For example, the facing adhesive 54 may be coated in a strip about the periphery of the facing substrate 52 or pattern coated on the facing substrate 52.

The release liner 60 may optionally be attached to the medical article 10 to protect the adhesives exposed on the front surface of the dressing. Examples of release liners are liners made of or coated with polyethylene, polypropylene and fluorocarbons, as well as silicone coated release papers or polymer films (e.g., polyester films, etc.). Examples of the silicone coated release papers are POLYSLIK S-8004, 83 pound (135.4 g/m$^2$) bleached silicone release paper supplied by H.P. Smith Co., Chicago, Ill., and 80 pound (130.5 g/m$^2$) bleached two-sided silicone coated paper (2-80-BKG-157) supplied by Daubert Chemical Co., Dixon, Ill.

Figure 2:
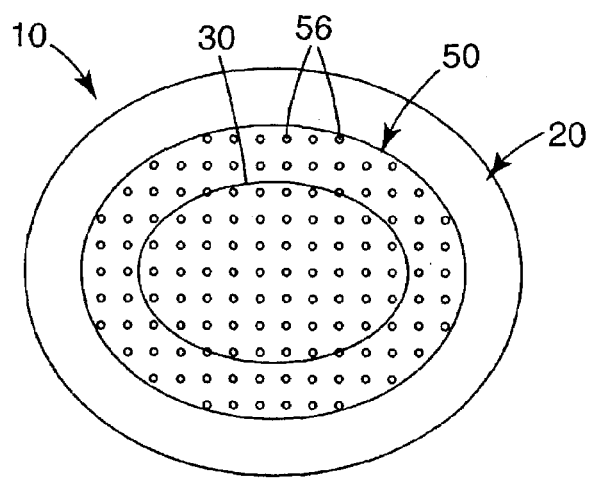
FIG. 2 is a plan view of the medical article of FIG. 1.

FIG. 2 is a plan view of the medical article 10 of FIG. 1 with the frame 26 removed from the backing layer 20. This view, in combination with FIG. 1, illustrates the relative sizes of the various components in the depicted embodiment. For example, the facing layer 50 occupies a smaller area than the backing layer 20. The backing layer 20 extends past the periphery of the facing layer 50 such that the backing layer 20 forms a frame about the periphery of the facing layer 50. It is preferred that the backing adhesive 24 be located within the area of the backing layer 20 that extends past the periphery of the facing layer 50 to, e.g., assist in retaining the medical article 10 on a patient.

Another relationship depicted in FIG. 2 is the relative size of the absorbent layer 30, which occupies a smaller area than the facing layer 50 as seen in FIG. 2. As a result, the facing layer 50 extends past the periphery of the absorbent layer 30 such that the facing layer 50 forms a frame about the absorbent layer 30. It is preferred that the back surface of the facing layer 50 be attached to the front surface of the backing layer 20 about the periphery of the absorbent layer 30. That attachment may be effected by the backing adhesive 24 or by any suitable technique or combination of techniques, e.g., heat sealing, ultrasonic welding, chemical welding, etc., and combinations thereof.

Although the phrase "about the periphery" as used in connection with the embodiment of FIGS. 1 & 2 means immediately adjacent the periphery as shown in FIGS. 1 & 2, that phrase also includes attachment of the two components at a distance outside of the periphery of the smaller component. For example, the facing layer 50 may be attached to the backing layer 20 only at its outermost periphery as opposed to immediately adjacent the periphery of the absorbent layer 30.

By providing backing layer 20 that frames a facing layer 50, the outer portion of the medical article 10 may be more compliant and provide a lower edge profile than if the facing layer 50 extended out to the periphery of the backing layer 20. That improved compliance and lower profile can be beneficial in preventing unwanted detachment of the edge of the medical article from a patient due to stretching of the skin or friction from garments or bedding. Furthermore, moisture vapor permeability in the frame formed by the backing layer 20 may also be increased, thereby improving adhesion and comfort of the medical article.

Although not depicted in FIG. 2, the debonding agent 40 (see FIG. 1) may preferably be of a size roughly equal to the size of the absorbent layer 30. The debonding agent 40 may preferably be coextensive (i.e., the same size) as the absorbent layer 30 as seen in FIG. 1. Alternatively, the debonding agent 40 may occupy an area that is smaller or larger than the absorbent layer 30. It is preferred, however, that the debonding agent 40 occupy a smaller area than the facing layer 50, such that it does not interfere with proper attachment of the facing layer 50 to the backing layer 20 about the periphery of the absorbent layer.

The debonding agent 40 may be soluble or insoluble in the presence of water or wound exudate as discussed above. The debonding agent 40 may be provided in the form of a sheet or layer (as shown in FIG. 1) that is continuous or non-continuous. Examples of suitable sheet materials may include, but are not limited to, e.g., films, fabrics (e.g., woven, nonwoven, knit, etc.), foams, etc.

The water or wound exudate that causes detachment of the absorbent layer 30 from the backing layer 20 may preferably be associated with the absorbent layer 30 itself. As is described in more detail herein, the absorbent layer 30 as provided in a medical article of the present invention may preferably be substantially free of water before attachment to a patient. In use, however, the absorbent layer 30 absorbs water from, e.g., wound exudate or other sources. That water typically passes through the facing layer 50 to reach the absorbent layer 30.

It may be preferred that the debonding agent 40 cause detachment of at least a portion of the absorbent layer 30 from the backing layer 20 after the absorbent layer absorbs 200 wt-% water or more, preferably 100 wt-% water or more. Detachment may be the result of solubilization of the debonding agent in the presence of water in the absorbent layer 30.

In the embodiment depicted in FIG. 1, the debonding agent 40 may be provided in the form of a sheet that may be, e.g., constructed of a film, foam, fabric combination thereof that exhibits water solubility. Examples of water soluble films that may be used as a debonding agent in medical articles of the present invention include, but are not limited to, polyvinylpyrrolidone, polyvinylalcohol (e.g., made from polyvinyl acetate having a percent hydrolysis of 80%-100%, preferably 87%-100%, and more preferably 93%-100%), hydrophilic polyurethanes, hydrophilic hydroxyalkylesters of poly(meth) acrylic acid and copolymers thereof, hydrophilic polyether-polyamide polymers. Further examples of water soluble film materials include natural polymers and modified natural polymers such as cellulose derivatives (e.g., hydroxypropyl cellulose, hydroxyethyl cellulose, carboxymethylcellulose, etc.), guar, xantham gum, gelatin, etc. These materials may be provided alone or as blends, mixtures and laminates of two or more components. Such materials may be provided as films or foam sheets.

Although the layer 40 is depicted as continuous, it may include voids or apertures formed therein such that it could be considered to be a non-continuous component, that is, a component that does not completely cover the back surface of the absorbent layer 30.

It may be preferred that the debonding agent or layer 40 be attached to both the front surface of the backing layer 20 and the back surface of the absorbent layer 30 when the absorbent layer 30 is substantially free of water, thereby providing the desired operable attachment of the absorbent layer 30 to the backing layer 20.

Figure 3:
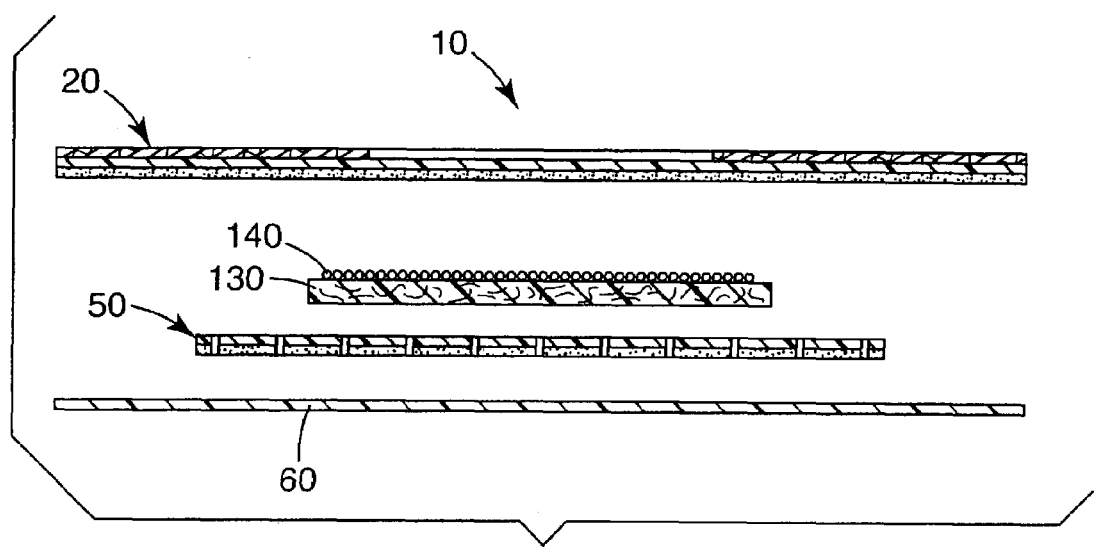
FIG. 3 is an exploded cross-sectional view of another illustrative embodiment of a medical article according to the present invention.

FIG. 3 depicts an alternative medical article 110 according to the present invention. Like medical article 10 of FIGS. 1 & 2, medical article 110 includes a backing layer 120, absorbent layer 130, facing layer 150 and optional release liner 160. The debonding agent 140, however, is not provided as a sheet article as seen in connection with FIGS. 1 & 2.

Rather, the medical article 110 includes a debonding agent 140 in the form of particulates located between the back surface of the absorbent layer 130 and the front surface of the backing layer 120. The particulates that serve as a debonding agent 140 in connection with the medical articles of the present invention may be water soluble or water insoluble. The particulates may take any physical form, e.g., granular, fibrous, microcapsules, beads, powders, etc.

The particulates may prevent contact between the absorbent layer and the backing layer in the interstices (if any) between particulates. Alternatively, the backing layer and the absorbent layer may be attached (e.g., adhered) to each other in the interstices between particulates. The particulates may serve as propagation points at which detachment of the absorbent layer from the backing layer begins when the absorbent layer takes up sufficient water from, e.g., wound exudate, etc.

The particulates of debonding agent may all have the same composition or different compositions. If particulates with different compositions are used, some of the particulates may be water soluble while other particulates may be water insoluble. Examples of some suitable particulates that may be used in connection with medical articles of the present invention may include, but are not limited to, e.g., inorganic particles such as colloidal silicon dioxide, organic particles such as carboxymethylcellulose, etc.

Debonding agents used in connection with the present invention may also include combinations of different articles and/or particulates provided that the desired detachment of the backing and the absorbent layer can be achieved in the presence of water. For example, the combination of one or more sheets and particulates may be used to achieve the desired detachment of the absorbent layer from the backing layer in medical articles according to the present invention.

Figure 4:
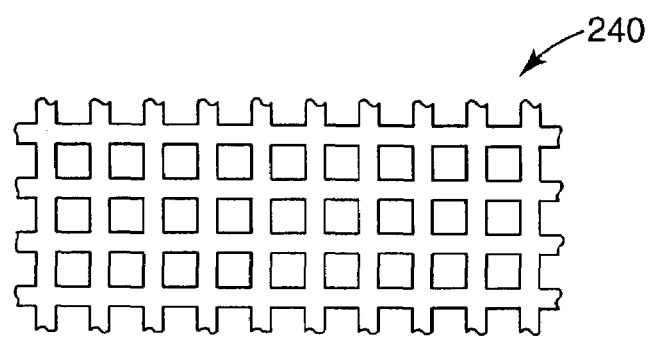
FIG. 4 is an exploded cross-sectional view of another illustrative embodiment of a medical article according to the present invention.

FIG. 4 is a plan view of a portion of another alternative for a debonding agent for use in connection with the present invention. The depicted alternative is netting 240 that may be interposed between the absorbent layer and the backing layer of a medical article according to the present invention. The netting 240 may prevent contact between the absorbent layer and the backing layer in the interstices between strands 242. Alternatively, the backing layer and the absorbent layer may be attached (e.g., adhered) to each other in the interstices between strands 242. The strands 242 may serve as propagation points at which detachment of the absorbent layer from the backing layer begins when the absorbent layer takes up sufficient water from, e.g., wound exudate, etc.

Regardless of the exact nature of the debonding agents used in connection with the present invention, it may be preferred that they do not significantly interfere with transparency of the medical article. For, example, the debonding agent itself may be transparent such as some of the films as described above. Alternatively, the debonding agents such as the particulates or netting discussed above may not themselves be transparent, but may provide sufficient interstices through which a wound or other surface may be adequately viewed.

FIGS. 5-10 illustrate various illustrative embodiments of medical articles according to the present invention in which a portion of the front surface of the backing substrate located directly opposite the absorbent layer is free of the backing adhesive. The adhesive free area or areas are provided in place of a physical debonding agent as described in connection with the embodiments of FIGS. 1-4, although in some instances it may be desirable to include both adhesive free areas and one or more physical debonding agents.

Figure 5:
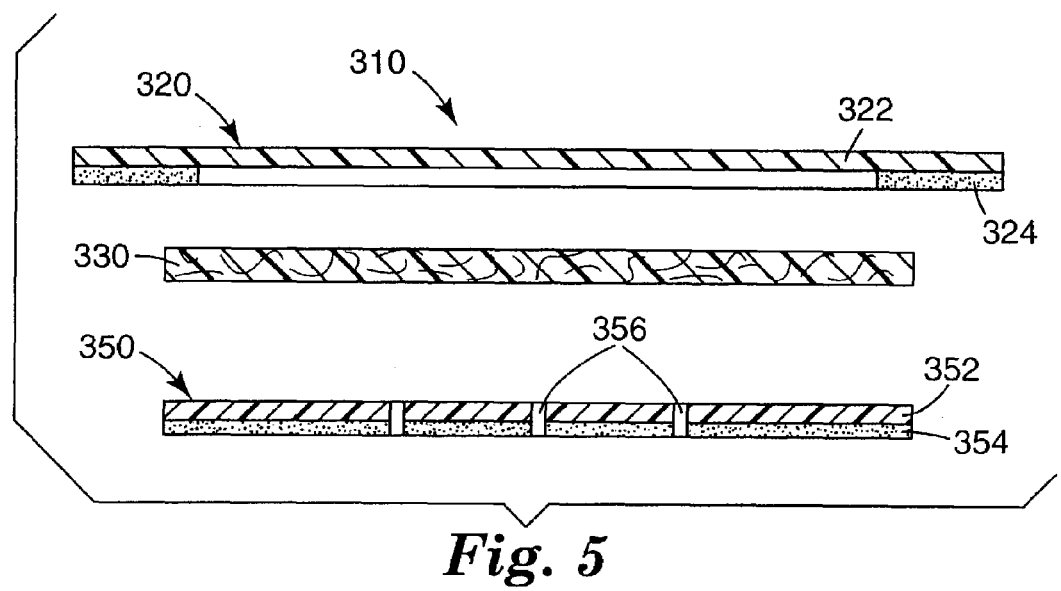
FIG. 5 is an exploded cross-sectional view of another illustrative embodiment of a medical article according to the present invention.
Figure 6:
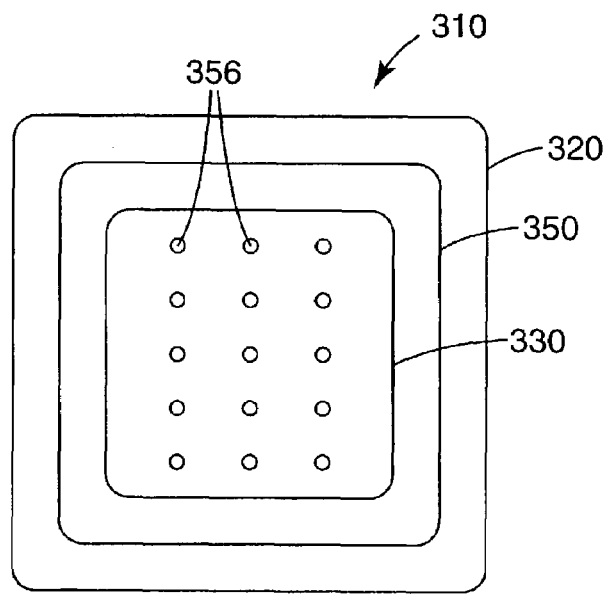
FIG. 6 is a plan view of the medical article of FIG. 5.

FIGS. 5 & 6 depict one embodiment of a medical article 310 that includes a backing substrate 322 and backing adhesive 324 that, together, provide a backing layer 320. An absorbent layer 330 is located between the backing substrate 322 and the facing layer 350 that includes a facing substrate 352 and optional facing adhesive 354. The facing layer 350 also includes optional openings 356 formed therethrough.

The backing adhesive 324 occupies an edge zone on the front surface of the backing substrate 322 surrounding the absorbent layer 330. In the depicted embodiment, the backing adhesive 324 is located between the absorbent layer 330 and the backing substrate 322 about the perimeter of the absorbent layer 330 such that the perimeter of the absorbent layer 330 is adhered to the backing substrate 322 by the backing adhesive 324. The central portion of the back surface of the absorbent layer 330 facing the backing substrate 322 is free of adhesive, thus allowing for volumetric expansion of the absorbent layer without the problems associated with swelling if the entire absorbent layer 330 were attached to the backing layer 320.

Figure 7:
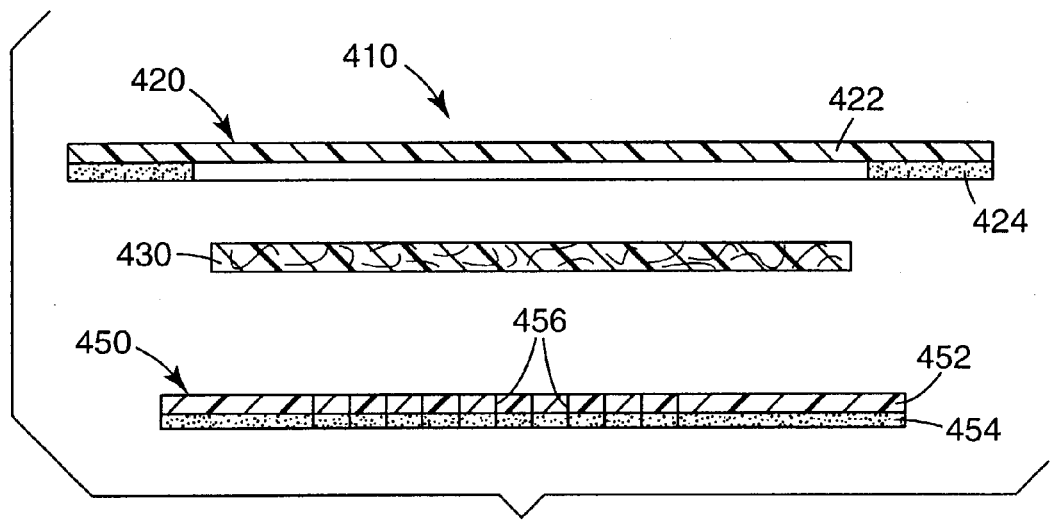
FIG. 7 is an exploded cross-sectional view of another illustrative embodiment of a medical article according to the present invention.
Figure 8:
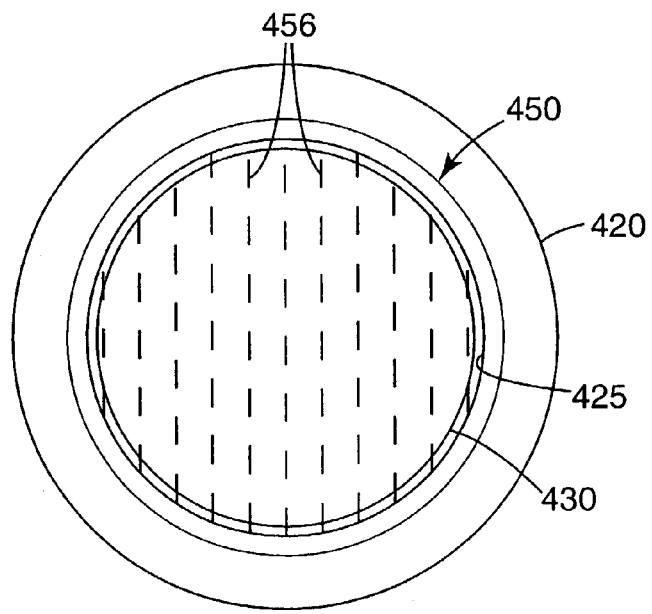
FIG. 8 is a plan view of the medical article of FIG. 7.

FIGS. 7 & 8 depict an embodiment of a medical article 410 that includes a backing substrate 422 and backing adhesive 424 that, together, provide a backing layer 420. An absorbent layer 430 is located between the backing substrate 422 and the facing layer 450 that includes a facing substrate 452 and optional facing adhesive 454. The facing layer 450 also includes optional openings 456 in the form of slits formed through the facing layer 450.

The backing adhesive 424 occupies an edge zone on the front surface of the backing substrate 422 surrounding the absorbent layer 430. In the depicted embodiment, the inner edge 425 of the backing adhesive 424 is located outside of the perimeter of the absorbent layer 430 such that none of the backing adhesive 424 is located between the absorbent layer 430 and the backing substrate 422. In other words, all of the front surface of the backing substrate 422 located directly opposite the absorbent layer 430 is free of the backing adhesive 424. As a result, volumetric expansion of the absorbent layer 430 can occur without the problems associated with swelling if the entire absorbent layer 430 were attached to the backing layer 420.

Figure 9:
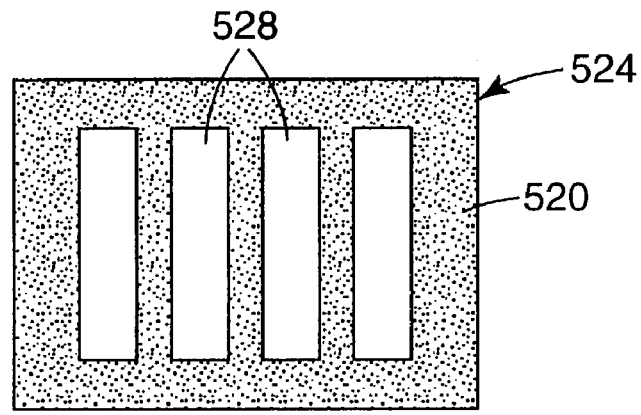
FIG. 9 is a plan view of the front surface of one backing layer pattern-coated with backing adhesive (with the facing layer and absorbent layer removed).

FIG. 9 depicts another variation that may be provided in connection with the present invention. Only the front surface of a backing layer 520 is depicted in FIG. 9 (i.e., the other components of the medical article have been removed). The backing adhesive 524 preferably occupies an edge zone about the perimeter of the backing layer 520. In addition, the backing adhesive 524 is strip coated on the backing layer 520, leaving areas or portions 528 of the backing layer 520 free of backing adhesive 524. The adhesive-free areas 528 may serve as points at which detachment of an absorbent layer (not shown) starts or propagates as the absorbent layer absorbs water, wound exudate, etc.

Figure 10:
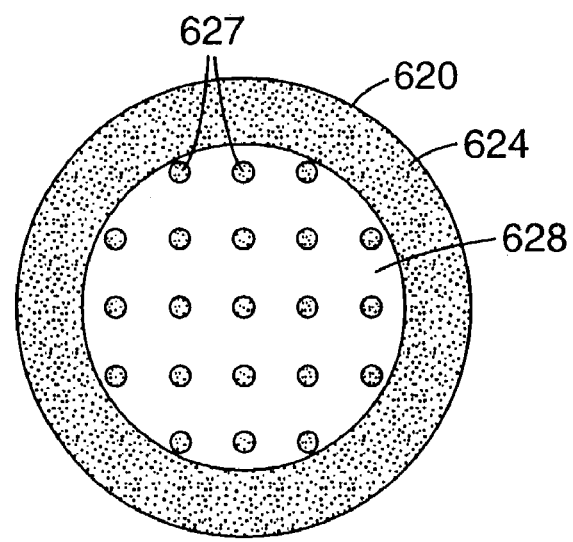
FIG. 10 is a plan view of the front surface of one backing layer pattern-coated with backing adhesive (with the facing layer and absorbent layer removed).

FIG. 10 depicts another variation that may be provided in connection with the present invention. As with FIG. 9, only the front surface of a backing layer 620 is depicted in FIG. 10 (i.e., the other components of the medical article have been removed). The backing adhesive 624 preferably occupies an edge zone about the perimeter of the backing layer 620. In addition, the backing adhesive is provided in one or more discrete areas 627 on the backing layer 620 such that the area 628 between the discrete areas 628 free of adhesive. The adhesive-free area 628 may serve as a point or points at which detachment of an absorbent layer (not shown) starts or propagates as the absorbent layer absorbs water, wound exudate, etc.

The following descriptions provide more specific considerations with respect to the facing layer, backing layer, adhesives and absorbent layers that may be advantageously used in medical articles according to the present invention.

A typical medical article, e.g., a wound dressing, of the present invention preferably includes an optional liquid permeable facing layer that provides a partial barrier between the wound site and the absorbent layer. The facing layer allows transport of moisture (i.e. fluid and vapor) from the wound to the absorbent layer and may isolate the wound from other components of the medical article.

The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. One preferred facing layer may be a polyurethane film.

In some embodiments, the continuous portion of the facing layer is conformable to animal (including human) anatomical surfaces, has a moisture vapor transmission rate (MVTR) of at least 300 grams per square meter per 24 hours at 80% relative humidity differential at 40° C. (per method of Chen, U.S. Pat. No. 5,733,570), is impermeable to liquid water. Such a facing layer does, however, include openings through which wound exudate can pass. This means that the facing layer may not pass liquid water under normal wound treatment conditions except at the places in the facing layer that are slit, perforated, or otherwise modified to allow the exudate to pass into the absorbent layer. The preferred moisture vapor transmission rate of the continuous portion of the facing layer may be at least 600 grams per square meter per 24 hours at an 80% relative humidity differential at 40° C.

The facing layer may further include a pressure sensitive adhesive layer as depicted in, e.g., FIG. 1. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyether-amide, polyurethanes, chlorinated polyethylene, styrene/butadiene block copolymers (KRATON brand thermoplastic rubber, Shell Chemical Company, Houston, Tex.) and poly(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforations, slits, etc. that provide for passage of liquids through the facing layer may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the absorbent layer and into which the exudate from the wound passes. This reservoir preferably does not permit liquid water or exudate that enters the reservoir to exit the reservoir. Instead, the absorbent layer absorbs the exudate, and moisture in the exudate passes through the backing layer in a vapor form into the atmosphere. The reservoir dressing permits wound exudate to be rapidly removed from the wound site and prevents liquids or bacteria outside the dressing from contaminating the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful as facing or backing layers include polyurethanes such as those available under the trade designation ESTANE from B.F. Goodrich, Cleveland, Ohio, elastomeric polyester such as those available under the trade designation HYTREL from E.I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films may include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 g/m$^2$/24 hrs, preferably about 3000 to 4000 g/m$^2$/24 hrs. A particularly preferred spyrosorbent film, useful as a backing layer, is a segmented polyurethane such as a segmented polyether polyurethane urea based on polytetramethylene glycol and polyethylene glycol polyols. Examples of spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in International Publication No. WO 00/42958.

As discussed above, it is preferred that the medical articles of the present invention be transparent so that the wound site to which they are applied can be viewed through the medical article. Preferred films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. Nos. 4,499,896 (Heinecke); 4,598,004 (Heinecke); and 5,849,325 (Heinecke et al).

While the facing layer can be attached to the wound by means other than a pressure sensitive adhesive on its surface, it is preferred to use such an adhesive. The presence of the adhesive on the facing layer normally reduces the moisture vapor permeability of the facing layer. Therefore, it is preferred that the facing layer is adhesive coated prior to adding perforations or slits to the layer. The wound exudate therefore can readily pass through a perforated or slit adhesive coated facing layer. Preferably, both the facing and backing layers are precoated with an adhesive layer to both facilitate bonding of the backing layer to the facing layer (forming a pouch), and bonding of the facing film to the wound site.

The adhesive on the facing layer can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that include block copolymers having three or more polymer block structures having a general configuration -A-B-A- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), and International Publication Nos. WO 99/13866 and WO 99/13865; multilayered adhesives as disclosed in U.S. Pat. Publication No. 2001/0051178 A1 (Blatchford et al.). A particularly preferred adhesive includes 15 wt-% acrylic acid, 15 wt-% methoxypolyethylene oxide 750 acrylate, 70 wt-% isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the absorbent layer, e.g., the adhesive may be coated at the periphery of the wound dressing. Alternatively, the adhesive layer may be perforated slit or otherwise modified for the facing layer to provide a fluid path for the exudate.

The absorbent layers used in medical articles of the present invention is advantageously transparent. For medical articles in the form of wound dressings, this allows for visual inspection of the wound without removal of the wound dressing. Preferably, the absorbent layer is transparent whether dry or swollen with an aqueous solution (e.g., bodily fluid). Preferably, herein, transparent refers to a material having a total light transmittance of greater than 84% per ASTM D1003-00.

The absorbent layer includes absorbent material that is capable of absorbing fluids, preferably moderate to heavy amounts of fluids such as body fluids, while retaining the structural integrity (and preferably transparency) of the absorbent layer as a whole. Preferably, herein, "absorbent" refers to a material that will absorb at least its own weight of an isotonic saline solution (0.9 wt-% sodium chloride in deionized water) after 24 hours at room temperature. That is, the material has an absorbency of at least 100 wt-%. More preferably, the absorbent material in the absorbent layer can absorb at least two times its weight (200 wt-% absorbency), even more preferably at least four times its weight (400 wt-% absorbency), and most preferably at least five times its weight (500 wt-% absorbency) of an isotonic saline solution after 24 hours at room temperature.

Preferred absorbent layers of the present invention are also relatively flexible. Flexibility allows for a medical article incorporating the absorbent layer to be easily applied to a bend portion of a body, such as a joint, etc. Nonflexible absorbent layers are also within the scope of the present invention.

The absorbent layers of the present invention are also preferably biocompatible. Herein, "biocompatible" means that the material can be in contact with bodily tissues (including fluids) without adverse reactions. Typically, this occurs if, e.g., the residual monomers used to prepare a polymer used in the absorbent layer are present in less than about 1 percent by weight (wt-%) each, based on the total weight of the polymer.

The absorbent layer of the present invention can also possess pressure sensitive adhesive properties. The pressure sensitive adhesives of the invention are polymers exhibiting a glass transition temperature of less than −15° C.

Preferably, the absorbent layers used in the present invention are inherently bacteriostatic and possesses low odor. Alternatively, bacteriostatic or odor removing agents can be added to the absorbent layer or other components in the medical article to enhance these properties.

The absorbent layers of the present invention can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product (if any) of the absorbent layer is cured as long as they do not interfere with polymerization of the polymer. Preferably, they are added in an amount or manner that does not interfere with the function or clarity of the finished absorbent layer.

Although the absorbent layer may preferably be constructed of the gel materials described in greater detail herein, the absorbent layer may be constructed of hydrocolloids. Optionally, the absorbent layer may be constructed primarily of the gel materials, but incorporate hydrocolloids, typically in the form of particles. The use of hydrocolloids is, however, not necessarily preferred since hydrocolloids can limit the transparency of the absorbent layer.

Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. If used in connection with the gel materials described herein, the amount of the hydrocolloid is limited such that the absorbent layer, as a whole, is transparent (preferably, the total light transmittance is greater than 84% per ASTM D1003-00) after absorbing 100 wt-% isotonic saline solution. The amount of hydrocolloid, if used in connection with the gel material, may preferably be less than about 5 wt-%, based on the total weight of the gel material.

Other additives that can be incorporated into the absorbent layer of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and alpha-methylstyrene, the latter of which can also be a hydrophobic monomer as discussed herein); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the absorbent layer of the present invention is substantially free of plasticizers, including water. This is advantageous at least because special packaging is not required. Furthermore, plasticizers can migrate to other parts of a dressing, for example, which can be detrimental to the integrity of the dressing, or into the body of the patient on which the dressing is disposed.

Optionally, the absorbent layer may have a patterned surface on at least one major surface thereof. The patterned surface may provide a larger surface area for absorption of wound exudate when oriented toward the wound surface, while reducing the absorbent surface area in direct or indirect contact with the wound. More significantly, the patterned surface may reduce the propensity of the absorbent layer to swell and push against the wound, reduce mushrooming (i.e. expansion of the absorbent layer through a porous film), limit premature separation of an adhesive layer from the skin, and/or enhance integrity of the material upon hydration.

The optional pattern imparted to the surface of the absorbent layer may be any suitable preselected three-dimensional pattern. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element may be advantageously chosen to present reduced surface area in contact with a wound or the facing film if present. The reduced surface area may further retard the tendency of the absorbent layer to swell into the wound, mushroom, or adhere to the wound site. Especially useful elements include pyramids, cones and truncated versions thereof, and ridges that are triangular in cross section. The elements may be random or non-random in the x-direction, the y-direction, or both. For ease of manufacture, it may be preferable that the pattern comprises a non-random array of elements disposed on the surface of the absorbent layer.

If desired, a pattern may also be imparted to the back surface of the absorbent layer (i.e., the major surface of the absorbent layer that faces away from the wound surface). Imparting such a pattern may increase the surface area of the absorbent layer and may promote greater evaporation of the fluid from the absorbent layer. The pattern may be the same or different than the pattern on the opposite surface of the absorbent layer, as can the size of the pattern elements. Further, the individual elements on either surface of the absorbent layer may be protuberances extending form the surface, or may be depressions in the surface.

In a preferred medical article, the absorbent layer may have a thickness of 250 micrometers (i.e., microns) to about 5000 micrometers if constructed of the gel materials described herein.

Although the medical article is described and depicted as a single layer, the absorbent layer may, in fact, include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described herein prepared from the multifunctional macromonomer. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a the facing layer. By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 400 percent of its weight after immersion in an isotonic saline solution after 24 hours at room temperature.

The absorbent layers of medical articles according to the present invention may preferably include, or even consist essentially of (in some embodiments), a gel material of the present invention including a polymer, which can be a homopolymer or a copolymer, of a multifunctional poly (alkylene oxide) free-radically polymerizable macromonomer. The multifunctional poly(alkylene oxide) macromonomer has a weight average molecular weight of at least about 2000. Preferably, the multifunctional poly(alkylene oxide) macromonomer includes a copolymeric alkylene oxide moiety of the formula (Formula I):

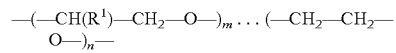

wherein the mole ratio of m:n is within a range of about 1:9 to about 9:1 (preferably, within a range of about 1:5 to about 1:1); and $R^1$ is a (C1-C4)alkyl group, which can be linear or branched. The distribution of the alkylene oxide moieties is random (i.e., there is a relatively random structural distribution of at least two different moieties). Such macromonomers are hydrophilic.

In the multifunctional macromonomers of Formula I, a ratio of below about 1:9 tends to render the material crystalline, whereas a ratio of greater than about 1:1 tends to reduce the absorbency of the material. Also, the longer the alkyl group ($R^1$), the lower the absorbency of the material. Preferably $R^1$ is a C1 alkyl and the copolymeric alkylene oxide moiety is a poly(ethylene oxide-co-propylene oxide).

The multifunctionality of the material leads to crosslinking upon polymerization. Typically, the higher the molecular weight, the greater the distance between crosslinks (i.e., the lower the crosslink density), which leads to better mechanical properties. That is, the gel materials of the present invention possess an advantageous balance of compliance (i.e., elasticity) and tensile strength as well as cohesive strength in the swollen form as a result of the use of the multifunctional poly(alkylene oxide) macromonomer.

The multifunctional macromonomer preferably has a weight average molecular weight of at least about 2000. Macromonomers with molecular weights lower than this tend to form brittle polymers. Preferably the multifunctional macromonomer has a weight average molecular weight of at least about 4000, more preferably at least about 6000, and most preferably at least about 10,000. Such materials can have significantly higher molecular weights as well. Preferably, such multifunctional macromonomers have a molecular weight such that they are flowable and processable at room temperature. High molecular weight multifunctional macromonomers that are not flowable at room temperature can be used if they can be processed using diluents or other additives and/or higher temperatures (e.g., extrusion temperatures). Most preferably, useful multifunctional macromonomers are liquid at room temperature.

Herein, multifunctional means that the macromonomer has more than one reactive group that is free radically polymerizable. Preferably, there are two or three reactive groups, and more preferably two reactive groups. Such multifunctional macromonomers can be linear or branched, preferably they are linear.

Preferably, the free radically polymerizable functionality of the multifunctional macromonomer includes ethylenic unsaturation. Examples of suitable ethylenically unsaturated groups include (meth)acryloyl, (meth)acrylamido, allyloxy, vinyl, etc., as well as combinations thereof. Alternatively, the reactive groups can include photoinitiator groups. Examples of photoinitiator groups include those derived from 1-[4-(2-hydroxyethoxy)phenyl]-2-hydroxy-2-methyl-1-propane-1-one (IRGACURE 2959) or any photoinitiator with a reactive nucleophilic group, such as 4-(2-hydroxyethoxy)benzophenone.

Preferably, the multifunctional macromonomer is difunctional. A particularly preferred difunctional macromonomer is of the formula (Formula II):

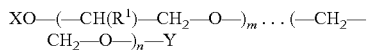

wherein: $R^1$, m, and n are as defined above; and X and Y are each independently selected from the group consisting of

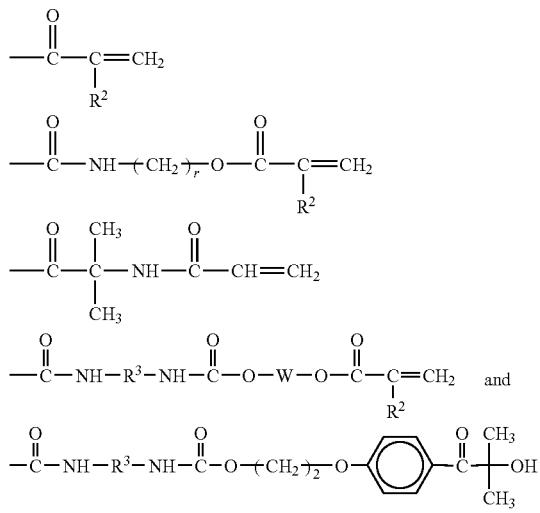

and wherein $R^2$ is H or $CH_3$, $R^3$ is an aromatic group, aliphatic group, alicylic group, or combinations thereof, W is an alkylene or alkylene oxide group, and r=2-10.

Preferably, the $R^3$ groups are derived from diisocyanates. More preferably, $R^3$ is selected from the group consisting of —$(CH_2)_p$— wherein p=1-18, tolylene, and

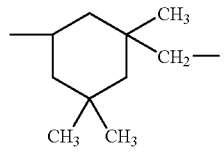

Most preferably, $R^3$ is derived from toluene diisocyanate, hexamethylene diisocyanate, or $H_{12}$-MDI (4,4'-methylene bis(cyclohexyl)diisocyanate).

Preferably, W is an alkylene or alkylene oxide containing up to 100 carbon atoms. More preferably, W is a group derived from an hydroxyalkyl (meth)acrylate.

As with Formula I, the alkylene oxide moieties of Formula II are preferably random. More preferably, it is a random poly(ethylene oxide-co-propylene oxide)-containing macromonomer.

The multifunctional macromonomers can also be tri-, tetra-, penta-functional, etc., macromonomers. Such compounds also include a copolymeric random alkylene oxide moiety of the formula:

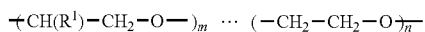

wherein the mole ratio of m:n is within a range of about 1:9 to about 9:1; and $R^1$ is a (C1-C4)alkyl group, and two or more end groups selected from the list of X and Y groups above. It should be understood that such end groups would be bonded through oxygen.

Multifunctional macromonomers can be linear with branched end groups or can be branched through a central core. Branched macromonomers can be prepared, for example, by chemical modification of linear dihydroxy terminated alkylene oxide random copolymers to produce multiple reactive end groups at each chain end. For example, a macromonomer with two polymerizable groups at each chain end can be prepared by reacting a linear dihydroxy terminated alkylene oxide random copolymer with trimellityl chloride followed by reaction with 2-hydroxyethyl methacrylate. Branch points in the macromonomer can also be introduced through incorporation of a central core. Examples of such materials include, but are not limited to, ethoxylated/propoxylated dipentaerythritol, pentaerythritol, and trimethyolpropane that have been further reacted with reactive ethylenically unsaturated compounds.

It should also be understood that each arm of a multifunctional macromonomer includes the copolymeric random alkylene oxide moiety, although each arm in any one macromonomer can be different. Also, there can be other groups or linkages, such as urethanes and/or urea groups between various copolymeric random alkylene oxide moieties in any one arm.

A particularly preferred macromonomer is of the formula

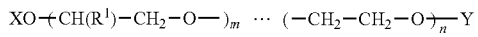

wherein $R^1$ is methyl, the mole ratio of m:n is about 1:3, and X and Y are each independently

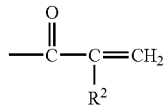

wherein $R^2$ is $CH_3$. This is referred to herein as MAA-PEG.

The functional macromonomers can be prepared, for example, by reacting dihydroxy terminated alkylene oxide random copolymers (which are typically commercially available such as poly(ethylene oxide-co-propylene oxide) commercially available as UCON-75H-90,000 from Dow Chemical Co., Midland, Mich.) with reactive ethylenically unsaturated compounds (e.g., acrylates) or photoinitiators. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. In addition, the dihydroxy terminated alkylene oxide random copolymer can be reacted with a diisocyanate, such as isophorone diisocyanate, resulting in an isocyanate terminated functional random copolymer that is further reacted with either functional (meth)acrylates or photoinitiators such as 2-hydroxyethyl (meth)acrylate or 1-[4-(2-hydroxyethoxy)phenyl]-2-hydroxy-2-methyl-1-propane-1-one. Preferably, the functional macromonomer is prepared by reacting the hydroxy terminated alkylene oxide random copolymer with methacrylic anhydride. Typically, if a stoichiometric amount of the ethylenically unsaturated reactant is combined with the dihydroxy terminated alkylene oxide random copolymer, 100% conversion to the disubstituted product is obtained. However, if less than a stoichiometric amount is used, the product is typically a mixture of disubstituted and monosubstituted products and possibly some dihydroxy terminated starting material. Such mixtures tend to provide gels with higher absorbency.

A multifunctional macromonomer as described herein can be homopolymerized or copolymerized with other multifunctional macromonomers or other hydrophilic monomers to enhance the absorbency of the polymer used in forming the gel material. Examples of suitable hydrophilic monomers include monofunctional poly(alkylene oxide) monomers and other polar monomers. The multifunctional macromonomer (or combination of macromonomers) can be copolymerized with hydrophobic monomers also to better control the absorbency of the polymer. Combinations of such hydrophilic and hydrophobic monomers can be used if desired.

Monofunctional poly(alkylene oxide) monomers can be used to increase the absorbency of the polymer used in forming the gel material. For certain preferred embodiments, such monomers can be analogous structurally to the multifunctional macromonomers described above with only one reactive group (e.g., only one (meth)acryloyl group, (meth)acrylamido group, allyloxy group), wherein the other end groups include nonreactive groups such as (C1-C4)alkoxy, aryloxy (e.g., phenoxy), (C1-C4)alkaryloxy, ar(C1-C4)alkyloxy, or hydroxy groups. These groups can be linear or branched.

Preferred monofunctional poly(alkylene oxide) monomers are of the formula (Formula III):

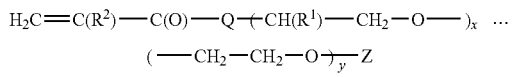

wherein the mole ratio of x:y is within a range of 0 to 1; $R^2$=H or $CH_3$; $R^1$ is as defined above for Formulas I and II; Z is H or a (C1-C4)alkyl group, an aryl group, a (C1-C4) alkaryl group, or an ar(C1-C4)alkyl group; and Q is —O—, —(H)N—C(CH$_3$)$_2$—C(O)—O—, —O—CH$_2$CH$_2$—N (H)—C(O)—O—, or

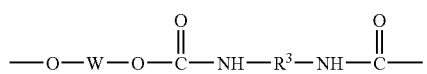

wherein $R^2$ is H or $CH_3$, $R^3$ is an aromatic group, aliphatic group, alicyclic group, or combinations thereof, and W is an alkylene or alkylene oxide group. These groups can be linear or branched. As with Formulas I and II, the alkylene oxide moieties are random (unless the ratio of x:y is 0). Such materials preferably have a weight average molecular weight of at least 200. Preferred $R^3$ and W groups are as described above. Preferably, Q is oxygen.

Examples of suitable monofunctional poly(alkylene oxide) monomers include poly(ethylene oxide)(meth)acrylate, poly(propylene oxide)(meth)acrylate, poly(ethylene oxide-propylene oxide)(meth)acrylate, and combinations thereof. Such monomers typically include nonreactive end groups such as (C1-C4)alkoxy, aryloxy (e.g., phenoxy), (C1-C4)alkaryloxy, ar(C1-C4)alkyloxy, or hydroxy groups. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

Polar monomers other than the poly(alkylene oxide) monomers can also be used to increase the absorbency of the polymer used in forming the gel material. Preferred polar monomers can also provide compliance to the resultant polymer. Examples of suitable polar monomers include 2-hydroxyethyl(meth)acrylate (HEMA), 2-hydroxypropyl(meth)acrylate, 3-hydroxypropyl(meth)acrylate, 4-hydroxybutyl (meth)acrylate, N-vinyl caprolactam, N-vinyl acetamide, N-vinyl pyrrolidone, acrylamide, mono- or di-N-alkyl substituted acrylamide, (meth)acrylic acid, itaconic acid, beta-carboxyethyl acrylate, glycerol methacrylate, [2-(meth)(acryloyloxy)ethyl]trimethylammonium chloride, [2-(meth)(acryloyloxy)ethyl]trimethylammonium methyl sulfate, and combinations thereof. Preferred polar monomers include 2-hydroxyethyl(meth)acrylate (HEMA) and N-vinyl pyrrolidone.

Hydrophobic monomers can be used to reduce (and thereby better control) the absorbency of the polymer used in forming the gel material, and preferably improve the strength of the polymer. Examples of suitable hydrophobic monomers include (meth)acrylic acid esters such as lauryl acrylate, 2-ethylhexyl acrylate, and isooctyl acrylate, as well as alpha-methylstyrene, and combinations thereof.

Preferred polymers used in forming the gel materials of the present invention include at least about 0.1 wt-% of the multifunctional poly(alkylene oxide) macromonomer, based on the total weight of the polymer. Practically, there is no upper limit to the amount of this multifunctional macromonomer that can be used. For example, homopolymers are possible, which could include 100 wt-% of any one multifunctional macromonomer. Preferred polymers for use in gel materials of the present invention include at least about 5 wt-% of the multifunctional poly(alkylene oxide) macromonomer, based on the total weight of the polymer. More preferably, the multifunctional poly(alkylene oxide) macromonomer is used in an amount of no greater than about 60 wt-%, based on the total weight of the polymer. Most preferably, the multifunctional poly(alkylene oxide) macromonomer is used in an amount of no greater than about 20 wt-%, based on the total weight of the polymer.

Preferred polymers used in forming the gel materials of the present invention include no greater than about 80 wt-% of a monofunctional poly(alkylene oxide) monomer, based on the total weight of the polymer. More preferably, the monofunctional poly(alkylene oxide) monomer is used in an amount of at least about 30 wt-%, based on the total weight of the polymer. Most preferably, the monofunctional poly(alkylene oxide) monomer is used in an amount of at least about 40 wt-%, based on the total weight of the polymer.

Preferred polymers used in forming the gel materials of the present invention include no greater than about 40 wt-% of a polar monomer, based on the total weight of the polymer. More preferably, the polar monomer is used in an amount of no greater than about 35 wt-%, based on the total weight of the polymer. Most preferably, the polar monomer is used in an amount of no greater than about 30 wt-%, based on the total weight of the polymer. Preferably, the polar monomer is used in an amount of at least about 5 wt-%, based on the total weight of the polymer. More preferably, the polar monomer is used in an amount of at least about 10 wt-%, based on the total weight of the polymer.

Preferred polymers used in forming the gel materials of the present invention include no greater than about 20 wt-% of a hydrophobic monomer, based on the total weight of the polymer. More preferably, the hydrophobic monomer is used in an amount of less than 20 wt-%, based on the total weight of the polymer. Even more preferably, the hydrophobic monomer is used in an amount of no greater than about 10 wt-%, based on the total weight of the polymer. Most preferably, the hydrophobic monomer is used in an amount of no greater than about 5 wt-%, based on the total weight of the polymer.

The polymer used in forming the gel material of the present invention (and preferably the gel material as well) is preferably substantially acid free. By this it is meant that no acidic monomers (e.g., (meth)acrylic acid, itaconic acid) are used in preparing the polymer in the gel material, although there may be certain acidic monomers present as contaminants in other monomers used. Thus, "substantially acid free" means that less than about 2 wt-% of the monomers used to prepare the polymer are acidic monomers.

The polymer used in forming the gel material of the present invention can be produced by polymerizing the above-described monomers by conventional polymerization methods. Typical polymerization methods that can be used include thermal and/or photochemical as well as bulk and solution polymerization.

In a typical solution polymerization method, a monomer mixture is heated with stirring in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and azobisisobutyronitrile. Those polymerization initiators can be used alone or as mixtures thereof.

In a typical photopolymerization method, a monomer mixture is irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819 and 2959.

A particularly preferred method of forming the polymer is described in U.S. patent application Ser. No. 10/121,489, filed on 12 Apr. 2002, titled METHOD OF MAKING A VISCOELASTIC ARTICLE BY COATING AND CURING ON A REUSABLE SURFACE.

Preferably, the method involves a "syrup polymer" technique, by which the polymer is dissolved in the component monomers, which react into the polymer backbone, further increasing the molecular weight. Molecular weight may be controlled through the use of chain transfer agents and chain retarding agents, as are known in the art, such as alkyl mercaptans such as dodecyl mercaptan, isooctyl thioglycolate, and alpha-methylstyrene.

The syrup polymer mixture preferably includes: about 0.1 wt-% to 100 wt-% of a solute polymer having terminal or pendant reactive free-radically curable functional groups (i.e., the multifunctional poly(alkylene oxide) macromonomer described above); 0 to about 80 wt-% of a monofunctional poly(alkylene oxide) monomer; 0 to about 40 wt-% of a polar monomer (distinct from the monofunctional poly (alkylene oxide) monomer); and 0 to about 20 wt-% of a hydrophobic monomer. Such a syrup is preferably partially polymerized (typically, about 10-15% conversion) to form a coatable composition (typically, having a viscosity of about 300 centipoise to about 20,000 centipoise), then coated onto a backing or a release liner, for example, and then polymerized further to form a gel. The syrup polymer mixture preferably includes a photoinitiator. The step of forming a gel from the syrup polymer mixture preferably includes applying radiation (infrared, ultraviolet, visible, electron beam, etc., preferably, ultraviolet radiation), thermal energy, or a combination thereof (preferably sequentially).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

The invention claimed is:

1. A medical article comprising:
   a backing layer comprising backing adhesive on a front surface of the backing layer;
   a liquid permeable facing layer;
   an absorbent layer located between the backing layer and the facing layer, wherein a back surface of the absorbent layer faces the front surface of the backing layer; and
   a water soluble film located between the front surface of the backing layer and the back surface of the absorbent layer;
   wherein the water soluble film layer causes detachment of at least a portion of the absorbent layer from the backing layer after the absorbent layer has absorbed water or wound exudate.

2. A medical article according to claim 1, wherein the water soluble film is coextensive with the back surface of the absorbent layer.

3. A medical article according to claim 1, wherein the water soluble film comprises a polyvinylalcohol film.

4. A medical article according to claim 1, wherein the water soluble film is a film selected from the group consisting of polyvinylpyrrolidone, polyvinylalcohol, hydrophilic polyurethanes, hydrophilic hydroxyalkylesters of poly(meth) acrylic acid and copolymers thereof, and hydrophilic polyether-polyamide polymers, as well as blends, mixtures and laminates thereof.

5. A medical article according to claim 1, wherein a back surface of the facing layer is operably attached to the front surface of the backing layer about a periphery of the absorbent layer.

6. A medical article according to claim 1, wherein the backing layer and the backing adhesive extend past a perimeter of the facing layer such that the backing layer and the backing adhesive form a frame about the periphery of the facing layer.

7. A medical article according to claim 1, wherein the backing layer and the backing adhesive extend past a perimeter of the facing layer such that the backing layer and the backing adhesive form a frame about the periphery of the facing layer, and wherein a back surface of the facing layer is operably attached to the front surface of the backing layer about a periphery of the absorbent layer.

8. A medical article according to claim 1, wherein the backing layer is moisture vapor permeable.

9. A medical article according to claim 1, wherein the facing layer comprises a moisture vapor permeable film.

10. A medical article according to claim 1, wherein the facing layer comprises a film that comprises a plurality of openings formed therethrough.

11. A medical article according to claim 1, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

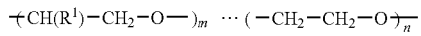

wherein the mole ratio of m:n is within a range of about 1:9 to about 9:1; and $R^1$ is a (C1-C4)alkyl group.

12. A medical article according to claim 1, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

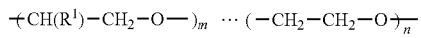

wherein the mole ratio of m:n is within a range of about 1:9 to about 9:1; and $R^1$ is a (C1-C4)alkyl group;
  a monofunctional poly(alkylene oxide) monomer; and
  a polar monomer.

13. A medical article according to claim 1, wherein the absorbent layer comprises a gel material comprising a homopolymer or copolymer prepared from monomers comprising about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

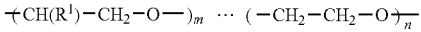

wherein the mole ratio of m:n is within a range of about 1:9 to about 9:1; and $R^1$ is a (C1-C4)alkyl group;
  0 wt-% to about 80 wt-% of a monofunctional poly(alkylene oxide) monomer; and
  0 wt-% to about 40 wt-% of a polar monomer.

14. A medical article according to claim 1, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

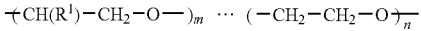

wherein the mole ratio of m:n is within a range of about 1:9 to about 9:1; and $R^1$ is a (C1-C4)alkyl group.

15. A medical article comprising:
  a backing layer comprising backing adhesive on a front surface of the backing layer;
  a liquid permeable facing layer;
  an absorbent layer located between the backing layer and the facing layer, wherein a back surface of the absorbent layer faces the front surface of the backing layer; and
  a debonding agent located between the front surface of the backing layer and the back surface of the absorbent layer;
  wherein the back surface of the absorbent layer is operably attached to the front surface of the backing layer before the medical article is applied to a patient, wherein at least a portion of the back surface of the absorbent layer is detached from the front surface of the backing layer when the absorbent layer has absorbed 100 wt-% or more of water, and wherein the combination of the backing layer, the facing layer, the absorbent layer, and the debonding agent are transparent when the absorbent layer has absorbed 100 wt-% of isotonic saline solution.

16. A medical article according to claim 15, wherein the debonding agent is water soluble.

17. A medical article according to claim 16, wherein the absorbent layer is substantially free of water before the medical article is applied to a patient.

18. A medical article according to claim 15, wherein the debonding agent is water soluble and further wherein the debonding agent comprises a layer that is coextensive with the back surface of the absorbent layer.

19. A medical article according to claim 15, wherein the debonding agent comprises water soluble particulates.

20. A medical article according to claim 15, wherein the debonding agent comprises a water insoluble structure.

21. A medical article according to claim 15, wherein the debonding agent comprises a fibrous structure.

22. A medical article according to claim 15, wherein the debonding agent comprises a water soluble foam layer.

23. A medical article according to claim 15, wherein a back surface of the facing layer is operably attached to the front surface of the backing layer about a periphery of the absorbent layer.

24. A medical article according to claim 15, wherein the backing layer and the backing adhesive extend past a perimeter of the facing layer such that the backing layer and the backing adhesive form a frame about the periphery of the facing layer.

25. A medical article according to claim 15, wherein the backing layer and the backing adhesive extend past a perimeter of the facing layer such that the backing layer and the backing adhesive form a frame about the periphery of the facing layer, and wherein a back surface of the facing layer is operably attached to the front surface of the backing layer about a periphery of the absorbent layer.

26. A medical article according to claim 15, wherein the debonding agent is operably attached to the back surface of the absorbent layer.

27. A medical article according to claim 15, wherein the debonding layer and the facing layer are operably attached to the backing layer by the backing adhesive.

28. A medical article according to claim 15, further comprising facing adhesive on a front surface of the facing layer.

29. A medical article according to claim 15, wherein the backing layer is moisture vapor permeable.

30. A medical article according to claim 15, wherein the facing layer comprises a moisture vapor permeable film.

31. A medical article according to claim 15, wherein the facing layer comprises a film that comprises a plurality of openings formed therethrough.

32. A medical article according to claim 15, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

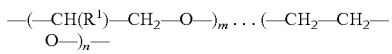

wherein the mole ratio of m:n is within a range of about 1:9 to about 9:1; and $R^1$ is a (C1-C4)alkyl group.

33. A medical article according to claim 15, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

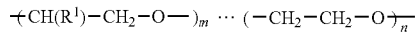

wherein the mole ratio of m:n is within a range of about 1:9 to about 9:1; and $R^1$ is a (C1-C4)alkyl group;
  a monofunctional poly(alkylene oxide) monomer; and
  a polar monomer.

34. A medical article according to claim 15, wherein the absorbent layer comprises a gel material comprising a homopolymer or copolymer prepared from monomers comprising about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

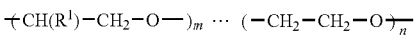

wherein the mole ratio of m:n is within a range of about 1:9 to about 9:1; and $R^1$ is a (C1-C4)alkyl group;
  0 wt-% to about 80 wt-% of a monofunctional poly(alkylene oxide) monomer; and
  0 wt-% to about 40 wt-% of a polar monomer.

35. A medical article according to claim 15, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

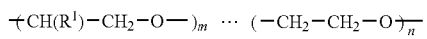

wherein the mole ratio of m:n is within a range of about 1:9 to about 9:1; and $R^1$ is a (C1-C4)alkyl group.

36. A medical article comprising:
  a moisture vapor permeable backing layer comprising backing adhesive on a front surface of the backing layer;
  a liquid permeable facing layer comprising a film that comprises a plurality of openings formed therethrough and facing adhesive on a front surface of the facing layer, wherein the backing layer and the backing adhesive extend past a perimeter of the facing layer such that the backing layer and the backing adhesive form a frame about the periphery of the facing layer;
  an absorbent layer located between the backing layer and the facing layer, wherein a back surface of the absorbent layer faces the front surface of the backing layer, wherein a back surface of the facing layer is attached to the front surface of the backing layer about a periphery of the absorbent layer, and wherein the absorbent layer is substantially free of water before the medical article is applied to a patient; and
  a water soluble debonding agent located between the front surface of the backing layer and the back surface of the absorbent layer;
  wherein the back surface of the absorbent layer is operably attached to the front surface of the backing layer before the medical article is applied to a patient, and wherein at least a portion of the back surface of the absorbent layer is detached from the front surface of the backing layer when the absorbent layer has absorbed 100 wt-% or more of water;
  and wherein the combination of the backing layer, the facing layer, the absorbent layer, and the debonding agent are transparent when the absorbent layer has absorbed 100 wt-% isotonic saline solution.

37. A medical article comprising:
  a backing layer comprising backing adhesive on a front surface of the backing layer;
  an absorbent layer located proximate the front surface of the backing layer, wherein a back surface of the absorbent layer faces the front surface of the backing layer; and
  a debonding agent located between the front surface of the backing layer and the back surface of the absorbent layer;

wherein the back surface of the absorbent layer is operably attached to the front surface of the backing layer before the medical article is applied to a patient, and wherein at least a portion of the back surface of the absorbent layer is detached from the front surface of the backing layer when the absorbent layer has absorbed 100 wt-% or more of water, and wherein the combination of the backing layer, the absorbent layer, and the debonding agent are transparent when the absorbent layer has absorbed 100 wt-% of isotonic saline solution.

38. A medical article according to claim 37, wherein the debonding agent is water soluble.

39. A medical article according to claim 37, wherein the absorbent layer is substantially free of water before the medical article is applied to a patient.

40. A medical article according to claim 37, wherein the debonding agent is water soluble and further wherein the debonding agent comprises a layer that is coextensive with the back surface of the absorbent layer.

41. A medical article according to claim 37, wherein the debonding agent comprises water soluble particulates.

42. A medical article according to claim 37, wherein the debonding agent comprises a water insoluble structure.

43. A medical article according to claim 37, wherein the debonding agent comprises a fibrous structure.

44. A medical article according to claim 37, wherein the debonding agent comprises a water soluble foam layer.

45. A medical article according to claim 37, wherein the backing layer and the backing adhesive extend past a perimeter of the absorbent layer such that the backing layer and the backing adhesive form a frame about the periphery of the absorbent layer.

46. A medical article according to claim 37, wherein the debonding layer is operably attached to the backing layer by the backing adhesive.

47. A medical article according to claim 37, wherein the backing layer is moisture vapor permeable.

48. A medical article according to claim 37, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

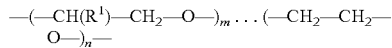

wherein the mole ratio of m:n is within a range of about 1:9 to about 9:1; and R¹ is a (C1-C4)alkyl group.

49. A medical article according to claim 37, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

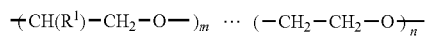

wherein the mole ratio of m:n is within a range of about 1:9 to about 9:1; and R¹ is a (C1-C4)alkyl group;
a monofunctional poly(alkylene oxide) monomer; and
a polar monomer.

50. A medical article according to claim 37, wherein the absorbent layer comprises a gel material comprising a homopolymer or copolymer prepared from monomers comprising about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

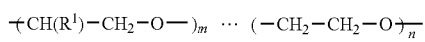

wherein the mole ratio of m:n is within a range of about 1:9 to about 9:1; and R¹ is a (C1-C4)alkyl group;
0 wt-% to about 80 wt-% of a monofunctional poly(alkylene oxide) monomer; and
0 wt-% to about 40 wt-% of a polar monomer.

51. A medical article according to claim 37, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

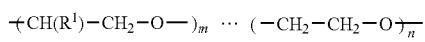

wherein the mole ratio of m:n is within a range of about 1:9 to about 9:1; and R¹ is a (C1-C4)alkyl group.

52. A medical article comprising:
a backing layer comprising backing adhesive on a front surface of the backing layer;
an absorbent layer located proximate the front surface of the backing layer, wherein a back surface of the absorbent layer faces the front surface of the backing layer; and
a debonding agent located between the front surface of the backing layer and the back surface of the absorbent layer;
wherein the back surface of the absorbent layer is operably attached to the front surface of the backing layer before the medical article is applied to a patient, and wherein at least a portion of the back surface of the absorbent layer is detached from the front surface of the backing layer when the absorbent layer has absorbed 100 wt-% or more of water, and wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

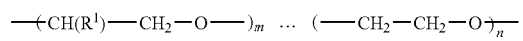

wherein the mole ratio of m:n is within a range of about 1:9 to about 9:1; and R¹ is a (C1-C4)alkyl group.

53. The medical article of claim 52, wherein the combination of the backing layer, the absorbent layer, and the debonding agent are transparent when the absorbent layer has absorbed 100 wt-% of isotonic saline solution.

54. A medical article according to claim 52, wherein the debonding agent is water soluble.

55. A medical article according to claim 52, wherein the absorbent layer is substantially free of water before the medical article is applied to a patient.

56. A medical article according to claim 52, wherein the debonding agent comprises a water insoluble structure.

57. A medical article comprising:
a backing layer comprising backing adhesive on a front surface of the backing layer;
an absorbent layer located proximate the front surface of the backing layer, wherein a back surface of the absorbent layer faces the front surface of the backing layer; and
a debonding agent located between the front surface of the backing layer and the back surface of the absorbent layer;
wherein the back surface of the absorbent layer is operably attached to the front surface of the backing layer before the medical article is applied to a patient, and wherein at least a portion of the back surface of the absorbent layer is detached from the front surface of the backing layer when the absorbent layer has absorbed 100 wt-% or more of water, and wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

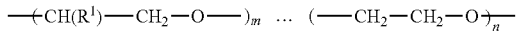

wherein the mole ratio of m:n is within a range of about 1:9 to about 9:1; and $R^1$ is a (C1-C4)alkyl group; a monofunctional poly(alkylene oxide) monomer; and a polar monomer.

58. The medical article of claim 57, wherein the combination of the backing layer, the absorbent layer, and the debonding agent are transparent when the absorbent layer has absorbed 100 wt-% of isotonic saline solution.

59. A medical article according to claim 57, wherein the debonding agent is water soluble.

60. A medical article according to claim 57, wherein the absorbent layer is substantially free of water before the medical article is applied to a patient.

61. A medical article according to claim 57, wherein the debonding agent comprises a water insoluble structure.

62. A medical article comprising:
a backing layer comprising backing adhesive on a front surface of the backing layer;
an absorbent layer located proximate the front surface of the backing layer, wherein a back surface of the absorbent layer faces the front surface of the backing layer; and
a debonding agent located between the front surface of the backing layer and the back surface of the absorbent layer;
wherein the back surface of the absorbent layer is operably attached to the front surface of the backing layer before the medical article is applied to a patient, and wherein at least a portion of the back surface of the absorbent layer is detached from the front surface of the backing layer when the absorbent layer has absorbed 100 wt-% or more of water, and wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

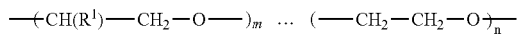

wherein the mole ratio of m:n is within a range of about 1:9 to about 9:1; and $R^1$ is a (C1-C4)alkyl group.

63. The medical article of claim 62, wherein the combination of the backing layer, the absorbent layer, and the debonding agent are transparent when the absorbent layer has absorbed 100 wt-% of isotonic saline solution.

64. A medical article according to claim 62, wherein the debonding agent is water soluble.

65. A medical article according to claim 62, wherein the absorbent layer is substantially free of water before the medical article is applied to a patient.

66. A medical article according to claim 62, wherein the debonding agent comprises a water insoluble structure.

67. A medical article comprising:
a backing layer comprising backing adhesive on a front surface of the backing layer;
a liquid permeable facing layer;
an absorbent layer located between the backing layer and the facing layer, wherein a back surface of the absorbent layer faces the front surface of the backing layer; and
a water soluble film located between the front surface of the backing layer and the back surface of the absorbent layer;
wherein the water soluble film is operably attached to the back surface of the absorbent layer.

68. A medical article according to claim 67, wherein the combination of the backing layer, the facing layer, the absorbent layer, and the water soluble film are transparent when the absorbent layer has absorbed 100 wt-% isotonic saline solution.

69. A medical article according to claim 67, wherein the water soluble film is coextensive with the back surface of the absorbent layer.

70. A medical article according to claim 67, wherein the water soluble film comprises a polyvinylalcohol film.

71. A medical article according to claim 67, wherein the water soluble film is a film selected from the group consisting of polyvinylpyrrolidone, polyvinylalcohol, hydrophilic polyurethanes, hydrophilic hydroxyalkylesters of poly(meth) acrylic acid and copolymers thereof, and hydrophilic polyether-polyamide polymers, as well as blends, mixtures and laminates thereof.

72. A medical article according to claim 67, wherein a back surface of the facing layer is operably attached to the front surface of the backing layer about a periphery of the absorbent layer.

73. A medical article according to claim 67, wherein the backing layer and the backing adhesive extend past a perimeter of the facing layer such that the backing layer and the backing adhesive form a frame about the periphery of the facing layer.

74. A medical article according to claim 67, wherein the backing layer and the backing adhesive extend past a perimeter of the facing layer such that the backing layer and the backing adhesive form a frame about the periphery of the facing layer, and wherein a back surface of the facing layer is operably attached to the front surface of the backing layer about a periphery of the absorbent layer.

75. A medical article according to claim 67, wherein the backing layer is moisture vapor permeable.

76. A medical article according to claim 67, wherein the facing layer comprises a moisture vapor permeable film.

77. A medical article according to claim 67, wherein the facing layer comprises a film that comprises a plurality of openings formed therethrough.

78. A medical article according to claim 67, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

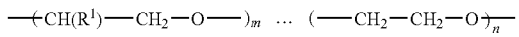

wherein the mole ratio of m:n is within a range of about 1:9 to about 9:1; and $R^1$ is a (C1-C4)alkyl group.

79. A medical article according to claim 67, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multi functional poly(alkylene oxide) macromonomer comprises a copolymeric alkylene oxide moiety of the formula:

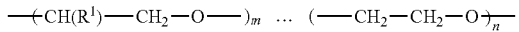

wherein the mole ratio of mm is within a range of about 1:9 to about 9:1; and $R^1$ is a (C1-C4)alkyl group;
a monofunctional poly(alkylene oxide) monomer; and
a polar monomer.

80. A medical article according to claim 67, wherein the absorbent layer comprises a gel material comprising a homopolymer or copolymer prepared from monomers comprising about 5 wt-% to 100 wt-% of a multifunctional poly (alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

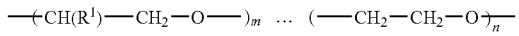

wherein the mole ratio of m:n is within a range of about 1:9 to about 9:1; and $R^1$ is a (C1-C4)alkyl group;
0 wt-% to about 80 wt-% of a monofunctional poly(alkylene oxide) monomer; and
0 wt-% to about 40 wt-% of a polar monomer.

81. A medical article according to claim 67, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

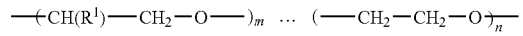

wherein the mole ratio of m:n is within a range of about 1:9 to about 9:1; and $R^1$ is a (C1-C4)alkyl group.

82. A medical article comprising:
a backing layer comprising backing adhesive on a front surface of the backing layer;
a liquid permeable facing layer;
an absorbent layer located between the backing layer and the facing layer, wherein a back surface of the absorbent layer faces the front surface of the backing layer; and
a water soluble film located between the front surface of the backing layer and the back surface of the absorbent layer;
wherein the water soluble film and the facing layer are operably attached to the backing layer by the backing adhesive.

83. A medical article according to claim 82, wherein the combination of the backing layer, the facing layer, the absorbent layer, and the water soluble film are transparent when the absorbent layer has absorbed 100 wt-% isotonic saline solution.

84. A medical article according to claim 82, wherein the water soluble film is coextensive with the back surface of the absorbent layer.

85. A medical article according to claim 82, wherein the water soluble film comprises a polyvinylalcohol film.

86. A medical article according to claim 82, wherein the water soluble film is a film selected from the group consisting of polyvinylpyrrolidone, polyvinylalcohol, hydrophilic polyurethanes, hydrophilic hydroxyalkylesters of poly(meth) acrylic acid and copolymers thereof, and hydrophilic polyether-polyamide polymers, as well as blends, mixtures and laminates thereof.

87. A medical article according to claim 82, wherein a back surface of the facing layer is operably attached to the front surface of the backing layer about a periphery of the absorbent layer.

88. A medical article according to claim 82, wherein the backing layer and the backing adhesive extend past a perimeter of the facing layer such that the backing layer and the backing adhesive form a frame about the periphery of the facing layer.

89. A medical article according to claim 82, wherein the backing layer and the backing adhesive extend past a perimeter of the facing layer such that the backing layer and the backing adhesive form a frame about the periphery of the facing layer, and wherein a back surface of the facing layer is operably attached to the front surface of the backing layer about a periphery of the absorbent layer.

90. A medical article according to claim 82, wherein the backing layer is moisture vapor permeable.

91. A medical article according to claim 82, wherein the facing layer comprises a moisture vapor permeable film.

92. A medical article according to claim 82, wherein the facing layer comprises a film that comprises a plurality of openings formed therethrough.

93. A medical article according to claim 82, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

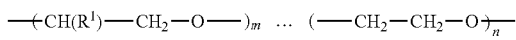

wherein the mole ratio of m:n is within a range of about 1:9 to about 9:1; and $R^1$ is a (C1-C4)alkyl group.

94. A medical article according to claim 82, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

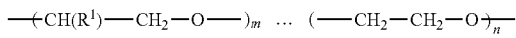

wherein the mole ratio of m:n is within a range of about 1:9 to about 9:1; and $R^1$ is a (C1-C4)alkyl group;
 a monofunctional poly(alkylene oxide) monomer; and
 a polar monomer.

95. A medical article according to claim 82, wherein the absorbent layer comprises a gel material comprising a homopolymer or copolymer prepared from monomers comprising about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

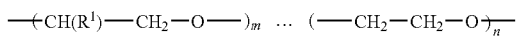

wherein the mole ratio of m:n is within a range of about 1:9 to about 9:1; and $R^1$ is a (C1-C4)alkyl group;
 0 wt-% to about 80 wt-% of a monofunctional poly(alkylene oxide) monomer; and
 0 wt-% to about 40 wt-% of a polar monomer.

96. A medical article according to claim 82, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

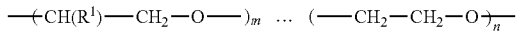

wherein the mole ratio of m:n is within a range of about 1:9 to about 9:1; and $R^1$ is a (C1-C4)alkyl group.

97. A medical article comprising:
 a backing layer comprising backing adhesive on a front surface of the backing layer;
 a liquid permeable facing layer comprising facing adhesive on a front surface of the facing layer;
 an absorbent layer located between the backing layer and the back surface of the facing layer, wherein a back surface of the absorbent layer faces the front surface of the backing layer; and
 a water soluble film located between the front surface of the backing layer and the back surface of the absorbent layer.

98. A medical article according to claim 97, wherein the combination of the backing layer, the facing layer, the absorbent layer, and the water soluble film are transparent when the absorbent layer has absorbed 100 wt-% isotonic saline solution.

99. A medical article according to claim 97, wherein the water soluble film is coextensive with the back surface of the absorbent layer.

100. A medical article according to claim 97, wherein the water soluble film comprises a polyvinylalcohol film.

101. A medical article according to claim 97, wherein the water soluble film is a film selected from the group consisting of polyvinylpyrrolidone, polyvinylalcohol, hydrophilic polyurethanes, hydrophilic hydroxyalkylesters of poly(meth) acrylic acid and copolymers thereof, and hydrophilic polyether-polyamide polymers, as well as blends, mixtures and laminates thereof.

102. A medical article according to claim 97, wherein a back surface of the facing layer is operably attached to the front surface of the backing layer about a periphery of the absorbent layer.

103. A medical article according to claim 97, wherein the backing layer and the backing adhesive extend past a perimeter of the facing layer such that the backing layer and the backing adhesive form a frame about the periphery of the facing layer.

104. A medical article according to claim 97, wherein the backing layer and the backing adhesive extend past a perimeter of the facing layer such that the backing layer and the backing adhesive form a frame about the periphery of the facing layer, and wherein a back surface of the facing layer is operably attached to the front surface of the backing layer about a periphery of the absorbent layer.

105. A medical article according to claim 97, wherein the backing layer is moisture vapor permeable.

106. A medical article according to claim 97, wherein the facing layer comprises a moisture vapor permeable film.

107. A medical article according to claim 97, wherein the facing layer comprises a film that comprises a plurality of openings formed therethrough.

108. A medical article according to claim 97, wherein the absorbent layer comprises a gel material comprising a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

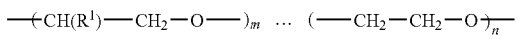

wherein the mole ratio of m:n is within a range of about 1:9 to about 9:1; and $R^1$ is a (C1-C4)alkyl group.

109. A medical article according to claim 97, wherein the absorbent layer comprises a gel material comprising a copolymer prepared from monomers comprising a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

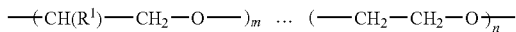

wherein the mole ratio of m:n is within a range of about 1:9 to about 9:1; and $R^1$ is a (C1-C4)alkyl group;
a monofunctional poly(alkylene oxide) monomer; and
a polar monomer.

110. A medical article according to claim 97, wherein the absorbent layer comprises a gel material comprising a homopolymer or copolymer prepared from monomers comprising about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

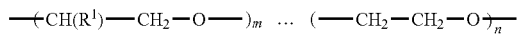

wherein the mole ratio of m:n is within a range of about 1:9 to about 9:1; and $R^1$ is a (C1-C4)alkyl group;
    0 wt-% to about 80 wt-% of a monofunctional poly(alkylene oxide) monomer; and
    0 wt-% to about 40 wt-% of a polar monomer.

111. A medical article according to claim 97, wherein the absorbent layer comprises a gel material comprising a polymerized multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

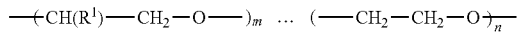

wherein the mole ratio of m:n is within a range of about 1:9 to about 9:1; and $R^1$ is a (C1-C4)alkyl group.

\* \* \* \* \*

UNITED STATES PATENT AND TRADEMARK OFFICE
CERTIFICATE OF CORRECTION

PATENT NO. : 7,612,248 B2
APPLICATION NO. : 10/324832
DATED : November 3, 2009
INVENTOR(S) : Scott A. Burton et al.

It is certified that error appears in the above-identified patent and that said Letters Patent is hereby corrected as shown below:

Column 6

Line 66; delete "METHODS." and insert -- METHODS (Attorney Docket No. 57001US002). --, therefor.

Column 7

Line 44; after "includes" delete "a" and insert -- the --, therefor.

Column 7

Line 56; delete "though" and insert -- through --, therefor.

Column 13

Line 67; delete "Altochem" and insert -- Atochem --, therefor.

Column 15

Line 57; delete "dichlofenac," and insert -- diclofenac, --, therefor.

Column 16

Line 16; delete "carrageenin)," and insert -- carrageenan), --, therefor.

Column 17

Line 67; delete "a the" and insert -- the --, therefor.

Column 20

Line 33-34; delete "trimethyolpropane" and insert -- trimethylolpropane --, therefor.

Column 22

Line 15; delete "Shinnakamura" and insert -- Shin Nakamura --, therefor.

Column 24

Line 2; delete "SURFACE." and insert -- SURFACE (Attorney Docket No. 56876US002). --, therefor.

CERTIFICATE OF CORRECTION (continued)
U.S. Pat. No. 7,612,248 B2

Column 33

Line 37; Claim 79, delete "mm" and insert -- m:n --, therefor.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,612,248 B2  Page 1 of 1
APPLICATION NO. : 10/324832
DATED : November 3, 2009
INVENTOR(S) : Burton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1887 days.

Signed and Sealed this

Nineteenth Day of October, 2010

David J. Kappos
*Director of the United States Patent and Trademark Office*